United States Patent
Gozes

(10) Patent No.: US 8,586,548 B2
(45) Date of Patent: Nov. 19, 2013

(54) NAP ALPHA-AMINOISOBUTYRIC ACID ANALOG WITH NEUROPROTECTIVE ACTIVITY

(75) Inventor: Illana Gozes, Ramat-Hasharon (IL)

(73) Assignee: Ramot at Tel-Aviv University, Ltd., Tel-Aviv (IL)

(*) Notice: Subject to any disclaimer, the term of this patent is extended or adjusted under 35 U.S.C. 154(b) by 0 days.

(21) Appl. No.: 13/390,770

(22) PCT Filed: Aug. 16, 2010

(86) PCT No.: PCT/IL2010/000660
§ 371 (c)(1),
(2), (4) Date: May 2, 2012

(87) PCT Pub. No.: WO2011/021186
PCT Pub. Date: Feb. 24, 2011

(65) Prior Publication Data
US 2012/0208763 A1    Aug. 16, 2012

Related U.S. Application Data

(60) Provisional application No. 61/234,396, filed on Aug. 17, 2009.

(51) Int. Cl.
*A61K 38/00* (2006.01)
*A61K 38/10* (2006.01)
*A61K 38/08* (2006.01)

(52) U.S. Cl.
USPC ....... 514/21.7; 514/21.4; 514/21.5; 514/21.6; 514/17.7; 514/17.8

(58) Field of Classification Search
None
See application file for complete search history.

(56) References Cited

U.S. PATENT DOCUMENTS 8,324,166 B2 * 12/2012 Gozes et al. ............ 514/17.7
2007/0142269 A1   6/2007 Lee et al.

FOREIGN PATENT DOCUMENTS

WO   WO/98/35042    * 2/1998 ........ C07K 14/475
WO   WO 2009/026687 A1   3/2009

OTHER PUBLICATIONS

Nuber et al. 2008 "Neurodegeneration and Motor Dysfunction in a conditional model of Parkinson's disease" J Neurosci 28(10):2471-2484.*
Sandri et al. 2004 "Foxo transcription factors induce the Atrophy-Related Ubiquitin Ligase Atrogin-1 and cause skeletal muscle atrophy" Cell 117(3):399-412.*
Rafii and Aisen 2009 "Recent developments in Alzheimer's disease therapeutics" BMC Medicine 7:7.*
Jaffe et al 2004 "The complete genome and proteome of Mycoplasma mobile" Genome Res 14:1447-1461 (abstract only).*
Uniprot Acession No. Q6KHH6. Last modified Jul. 5, 2004. Accessed May 3, 2013 from http://www.uniprot.org/uniprot/Q6Khh6.*
Gilead and Gazit 2004 "Inhibition of amyloid fibril formation by peptide analogues modified with alpha-aminoisobutyric acid" Angew Chem Int Ed 43:4041-4044.*

(Continued)

*Primary Examiner* — Jeffrey Stucker
*Assistant Examiner* — Adam M Weidner
(74) *Attorney, Agent, or Firm* — Kilpatrick Townsend & Stockton LLP

(57) ABSTRACT

The invention relates to compositions and methods to confer protection on neurons. Peptides derived from the NAPVSIPQ (SEQ ID NO:4) peptide and including branched amino acids, such as alpha-aminoisobutyric acid, are included. Also included are methods of preventing and treating neurodegenerative disorders and damage caused by neurotoxic substances.

8 Claims, 6 Drawing Sheets

(56) References Cited

OTHER PUBLICATIONS

Stains et al. 2007 "Molecules that target beta-amyloid" Chem Med Chem 2(12):1674-1692.*
Van Dijck et al. 2009 "NAP has no effect on spatial memory after short-term treatment in advanced stage Alzheimer's disease mouse model" Peptides 30:2480-2482.*
Pinhasov 2003 "Activity-dependent neuroprotective protein: a novel gene essential for brain formation" Dev Brain Res 144:83-90.*
International Search Report from PCT/IL2010/000660, dated Jan. 28, 2011(4 pages).
Friedhoff et al.; "Rapid Assembly of Alzheimer-like Paired Helical Filaments from Microtubule-Associated Protein Tau Monitored by Fluorescence in Solution"; *Biochemistry*; 37:10223-10230 (1998).
Perez et al.; "The role of the VQIVYK peptide in tau protein phosphorylation"; *Journal of Neurochemistry*; 103:1447-1460 (2007.
Von Bergen et al.; "Assembly of τ protein into Alzheimer paired helical filaments depends on a local sequence motif ($^{306}$VQIVYK$^{311}$.) β structure"; *Proceedings of the National Academy of Sciences USA*; 97(10):5129-5134 (2000).

* cited by examiner

Figure 1

NAP ALPHA-AMINOISOBUTYRIC ACID ANALOG WITH NEUROPROTECTIVE ACTIVITY

RELATED APPLICATIONS

This application is the U.S. National Stage entry under §371 of International Application No. PCT/IL2010/000660, filed Aug. 16, 2010, which claims priority to U.S. Provisional Patent Application No. 61/234,396, filed Aug. 17, 2009, the contents of each are incorporated by reference in the entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-9-3.TXT, created on Sep. 10, 2013, 28,672 bytes, machine format IBM-PC, MS-Windows operating system, is hereby incorporated by reference in its entirety for all purposes.

BACKGROUND OF THE INVENTION

NAP (NAPVSIPQ; SEQ ID NO:4) is derived from activity-dependent neuroprotective protein (ADNP) (Bassan et al., *J Neurochem*, 72(3):1283-93 (1999)), a protein that differentially interacts with chromatin to regulate genes essential for embryogenesis brain formation (Pinhasov et al., *Brain Res Dev Brain Res*, 144(1):83-90.2, 3 (2003); Mandel M., et al., *Developmental Biology*, (2006)). Furthermore, recombinant ADNP is neuroprotective in vitro against severe oxidative stress and neurotoxicity associated with the Alzheimer's disease neurotoxin, the beta amyloid peptide 25-35 (Steingart and Gozes, *Mol Cell Endocrinol*, 252(1-2):148-53 (2006)).

A number of neurodegenerative disorders are characterized by neurofibrillary tangles and amyloid deposits in the brain or central nervous system (CNS), including Alzheimer's disease, Parkinson's disease, and disorders related to diabetes. These deposits are formed by transition of native proteins into ordered beta sheet arrangements, and are toxic to the surrounding cells. Thus, agents that disrupt beta-sheet formation (i.e., beta sheet breakers or blockers) are useful for prevention and treatment of neurodegenerative disorders.

BRIEF SUMMARY OF THE INVENTION

The invention provides compositions and methods for protecting neuronal cells from neurotoxicity associated with chemical exposure and/or disease states. The invention is based on the surprising discovery that NAP alpha-aminoisobutyric acid peptides confer neuroprotection.

Accordingly, in some embodiments, the invention provides a NAP peptide with at least one amino acid substituted with a branched alkyl amino acid. For example, the substituted NAP peptide can have the formula: $(R^1)_a$-$(R^2)$-$(R^3)_b$ (SEQ ID NO:12-20), in which $R^2$ is a member selected from the group consisting of: NAXaaVSIXaaQ (SEQ ID NO:36), NXaaVSIPQ (SEQ ID NO:37), and NAPVSXaaQ (SEQ ID NO:38), wherein Xaa is a branched alkyl amino acid; $R^1$ is an amino acid sequence comprising from 1 to about 40 amino acids wherein each amino acid is independently selected from the group consisting of naturally occurring amino acids and amino acid analogs; $R^3$ is an amino acid sequence comprising from 1 to about 40 amino acids wherein each amino acid is independently selected from the group consisting of naturally occurring amino acids and amino acid analogs; and a and b are independently selected and are equal to zero or one; and wherein the substituted NAP peptide has neuroprotective activity. In some embodiments, the branched amino acid is selected from the group consisting of: alpha-aminoisobutyric acid, beta-aminoisobutyric acid, leucine, isoleucine, and valine.

Accordingly, in some embodiments, the invention provides a NAP-isobutyric acid (NAP-IBA) peptide, wherein the NAP-IBA peptide has the formula: $(R^1)_a$-$(R^2)$-$(R^3)_b$ (SEQ ID NOS:21-29), in which $R^2$ is a member selected from the group consisting of: NAXaaVSIXaaQ (SEQ ID NO:1), NXaaVSIPQ (SEQ ID NO:2), and NAPVSXaaQ (SEQ ID NO:3), wherein Xaa is alpha-aminoisobutyric acid; $R^1$ is an amino acid sequence comprising from 1 to about 40 amino acids wherein each amino acid is independently selected from the group consisting of naturally occurring amino acids and amino acid analogs; $R^3$ is an amino acid sequence comprising from 1 to about 40 amino acids wherein each amino acid is independently selected from the group consisting of naturally occurring amino acids and amino acid analogs; and a and b are independently selected and are equal to zero or one; and wherein the NAP-IBA peptide has neuroprotective activity.

In some embodiments, $R^2$ of the NAP-IBA peptide is SEQ ID NO:1. In some embodiments, $R^1$ is selected from the group consisting of: GG; LGG; and LGLGG (SEQ ID NO:9). In some embodiments, $R^3$ is QS.

In some embodiments, the sequence of the NAP-IBA peptide is selected from the group consisting of: GGNAXaaVSIXaaQ (SEQ ID NO:5); LGGNAXaaVSIXaaQQS (SEQ ID NO:6); LGLGGNAXaaVSIXaaQQS (SEQ ID NO:7); and SVALGLGGNAXaaVSIXaaQQS (SEQ ID NO:8), wherein Xaa is alpha-aminoisobutyric acid.

In some embodiments, the sequence of the NAP-IBA peptide includes at least one D amino acid. In some embodiments, the sequence of the NAP-IBA peptide includes 2, 3, 4, 5, 6 or more D amino acids.

In some embodiments, the NAP-IBA peptide includes a covalently-bound lipophilic moiety. In some embodiments, the lipophilic moiety is bound to the C terminus, while in other embodiments, it is bound to the N-terminus of the peptide. In some embodiments, more than one lipophilic moiety is bound to the NAP-IBA peptide, e.g., at both the N- and C-termini, or throughout the sequence. In some embodiments, an acetyl group, an amide group, or both, can be bound to the NAP-IBA peptide to inhibit degradation. Generally, the acetyl group is added to the C-terminus of the peptide, while the amide group is added to the N-terminus.

In some embodiments, the invention provides a pharmaceutical composition comprising a NAP-IBA peptide. In some embodiments, the pharmaceutical composition further comprises a physiologically acceptable excipient. Optionally, the composition also includes the NAP peptide (SEQ ID NO:4), such that the NAP peptide and the NAP-IBA peptide may be administered in combination.

The invention also provides methods of treating and preventing disorders associated with neurotoxicity or neurodegeneration in a subject. Such methods comprise the step of administering a therapeutically effective amount of a NAP-IBA peptide to a subject in need thereof. In some embodiments, the disorder is selected from the group consisting of: a neurodegenerative disorder, a cognitive deficit, an autoimmune disorder, peripheral neurotoxicity, motor dysfunction, sensory dysfunction, anxiety, depression, psychosis, a condition related to fetal alcohol syndrome, a condition involving retinal degeneration, a disorder affecting learning and memory, or a neuropsychiatric disorder.

In some embodiments, the NAP-IBA peptide is administered to the subject intranasally. In some embodiments, the NAP-IBA peptide is administered to the subject intravenously. In some embodiments, the NAP-IBA peptide is administered to the subject orally. In yet other embodiments, the NAP-IBA peptide may be administered in combination with the NAP peptide, which has the amino acid sequence of SEQ ID NO:4.

BRIEF DESCRIPTION OF THE DRAWINGS

FIG. 1 is a graphical depiction of neuronal cell numbers, as a percentage of control, in the presence of increasing amounts of alpha-aminoisobutric NAP (SEQ ID NO:1) and 2.5 micromolar beta amyloid peptide. The results demonstrate that alpha-aminoisobutric NAP confers protection of neurons the toxic effects of beta amyloid peptide. *** indicates p<0.001.

DETAILED DESCRIPTION OF THE INVENTION

A. Definitions

Figure 2:
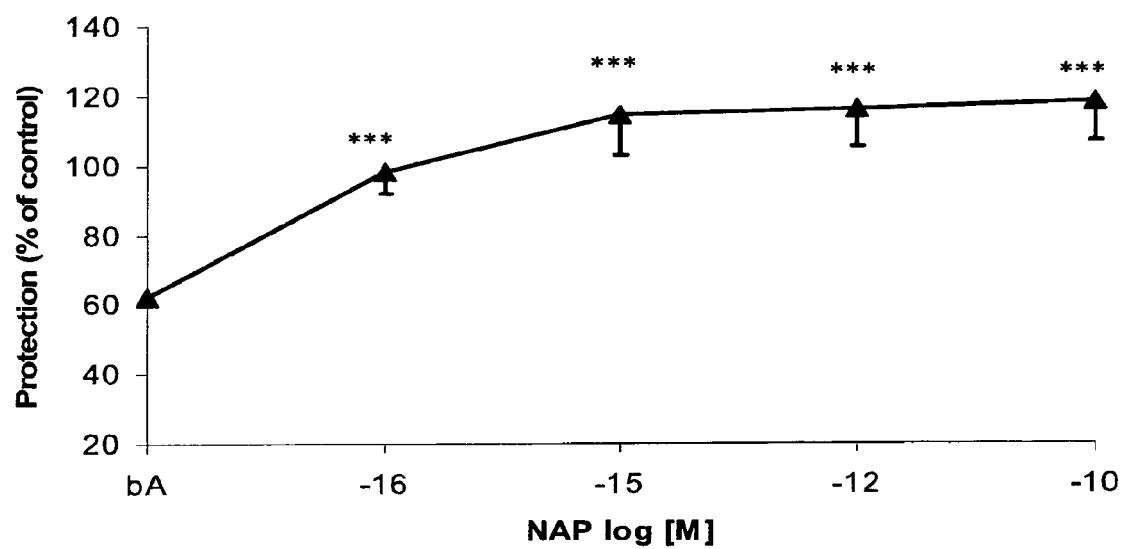
FIG. 2 is a graphical depiction of neuronal cell numbers, as a percentage of control, in the presence of increasing amounts of unmodified NAP and 2.5 micromolar beta amyloid peptide. Comparison to FIG. 1 indicates that alpha-aminoisobutyric NAP has increased neuroprotective activity. *** indicates p<0.001.

The phrases "NAP-isobutyric acid peptide," "NAP-aminoisobutyric acid peptide," and "NAP-IBA peptide" refer to an agent derived from NAPVSIPQ (SEQ ID NO:4; i.e., NAP), where at least one amino acid, preferably proline, is substituted with alpha-aminoisobutyric acid. Examples of NAP-IBA peptides are described in SEQ ID NOs:1-8. As used herein, "Alpha-aminoisobutyric NAP" refers to the sequence NAXaaVSIXaaQ (SEQ ID NO:1), wherein Xaa is alpha-aminoisobutyric acid. In this case, proline is substituted with alpha-aminoisobutyric acid (Gilead S. & Gazit E. (2004) *Angew Chem Int Ed Engl.,* 43:4041-4044). However, in some embodiments, NAP-IBA peptides include sequences with at least one substitution of any amino acid of the NAPVSIPQ (SEQ ID NO:4) core peptide.

As used herein, the phrase "NAP peptide" or "NAP analog" refers to an agent derived from NAPVSIPQ (SEQ ID NO:4; i.e., NAP), where at least one amino acid, preferably proline, is substituted with a branched alkyl amino acid. Branched alkyl amino acids include alpha-aminoisobutyric acid, beta-aminoisobutyric acid, leucine, isoleucine, and valine. For example, a NAP peptide or NAP analog can have the sequence of: NAXaaVSIXaaQ (SEQ ID NO:36), NXaaVSIPQ (SEQ ID NO:37), or NAPVSXaaQ (SEQ ID NO:38), wherein Xaa is a branched alkyl amino acid.

The phrase "ADNF polypeptide" refers to one or more activity dependent neurotrophic factors (ADNF), also called activity-dependent neuroprotective proteins (ADNP), that have an active core site comprising the amino acid sequence of NAPVSIPQ ((SEQ ID NO:4) referred to as "NAP") or SALLRSIPA ((SEQ ID NO:11) referred to as "SAL"), or conservatively modified variants thereof that have neurotrophic/neuroprotective activity as measured with in vitro cortical neuron culture assays described by, e.g., Hill et al., *Brain Res.* 603:222-233 (1993); Brenneman & Gozes, *J. Clin. Invest.* 97:2299-2307 (1996), Forsythe & Westbrook, *J. Physiol. Lond.* 396:515 (1988). An ADNF polypeptide can be an ADNF I polypeptide, an ADNF III polypeptide, their alleles, polymorphic variants, analogs, interspecies homolog, any subsequences thereof (e.g., SALLRSIPA (SEQ ID NO:11) or NAPVSIPQ (SEQ ID NO:4)) or lipophilic variants that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The phrase "ADNF III polypeptide" or "ADNF III" refers to one or more activity dependent neurotrophic factors (ADNF) that have an active core site comprising the amino acid sequence of NAPVSIPQ ((SEQ ID NO:4); NAP), or conservatively modified variants thereof that have neurotrophic/neuroprotective activity as measured with in vitro cortical neuron culture assays described by, e.g., Hill et al., *Brain Res.* 603, 222-233 (1993); Gozes et al., *Proc. Natl. Acad. Sci. USA* 93, 427-432 (1996). An ADNF polypeptide can be an ADNF III polypeptide, allelelic or polymorphic variant, analog, interspecies homolog, or any subsequences thereof that exhibits neuroprotective/neurotrophic action on, e.g., neurons originating in the central nervous system either in vitro or in vivo. ADNF III polypeptides can range from about eight amino acids and can have, e.g., between 8-20, 8-50, 10-100 or about 1000 or more amino acids.

Full length human ADNF III has a predicted molecular weight of 123,562.8 Da (>1000 amino acid residues) and a pI of about 6.97. As described above, ADNF III polypeptides have an active site comprising an amino acid sequence of Asn-Ala-Pro-Val-Ser-Ile-Pro-Gln ("NAPVSIPQ" or "NAP" (SEQ ID NO:4)). See Zamostiano et al., *J. Biol. Chem.* 276: 708-714 (2001) and Bassan et al., *J. Neurochem.* 72:1283-1293 (1999). Unless indicated as otherwise, "NAP" refers to a peptide having an amino acid sequence of Asn-Ala-Pro-Val-Ser-Ile-Pro-Gln (SEQ ID NO:4), not a peptide having an amino acid sequence of Asn-Ala-Pro. Full-length amino acid and nucleic acid sequences of ADNF III can be found in WO 98/35042, WO 00/27875, U.S. Pat. Nos. 6,613,740 and 6,649, 411. The Accession number for the human sequence is NP 852107, see also Zamostiano et al., supra.

The term "subject" refers to any mammal, in particular human, at any stage of life.

The term "contacting" is used herein interchangeably with the following: combined with, added to, mixed with, passed over, incubated with, flowed over, etc. Moreover, the polypeptides or nucleic acids of the present invention can be "administered" by any conventional method such as, for example, parenteral, oral, topical, nasal, ocular, and inhalation routes. In some embodiments, parenteral and nasal or inhalation routes are employed.

The term "biologically active" refers to an agent that will interact with naturally occurring biological molecules to either activate or inhibit the function of those molecules in vitro or in vivo. The term "biologically active" is most commonly used herein to refer to agents that exhibit neuroprotective/neurotrophic action on neurons originating in the central nervous system both in vitro or in vivo. Thus, the present invention provides agents and polypeptide subsequences that have the same or similar activity as NAP when tested, e.g., on cerebral cortical cultures treated with a neurotoxin (see Gozes et al., *Proc. Nat'l. Acad. Sci. USA* 93:427-432 (1996)). The peptides can also be tested as described herein to determine their ability to enhance cell survival, e.g., by 2-10%, by 10-50%, by 50-100%, or by more than 100%.

The phrase "neurodegenerative disorders or cognitive defects" includes, but is not limited to the following conditions:

Diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

Diseases affecting sensory neurons such as Friedreich's ataxia, diabetes, peripheral neuropathy, retinal neuronal degeneration;

Diseases of limbic and cortical systems such as cerebral amyloidosis, Pick's atrophy, Retts syndrome;

Neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration, corticobasal degeneration and progressive supranuclear palsy;

Pathologies associated with developmental retardation and learning impairments, Down's syndrome, and oxidative stress induced neuronal death;

Pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

Pathological changes resulting from focal trauma such as stroke, focal ischemia, vascular insufficiency, hypoxic-ischemic encephalopathy, hyperglycemia, hypoglycemia, closed head trauma, or direct trauma;

Pathologies arising as a negative side effect of therapeutic drugs and treatments (e.g., degeneration of cingulate and entorhinal cortex neurons in response to anticonvulsant doses of antagonists of the NMDA class of glutamate receptor).

"Peripheral neurotoxicity" may be identified and diagnosed in a subject by a variety of techniques. Typically it may be measured by motor dysfunction, muscle wasting, or a change in sense of smell, vision or hearing, or changes in deep tendon reflexes, vibratory sense, cutaneous sensation, gait and balance; muscle strength, orthostatic blood pressure, and chronic or intermittent pain. In humans these symptoms are also sometimes demonstrative of toxic effects in both the PNS and the CNS. Reflecting the scope of PNS activity, symptoms may involve sensory, motor, or autonomic functions. They can be classified according to the type of affected nerves and how long symptoms have been developing. Peripheral neurotoxicity can be induced by chemotherapeutic agents (anti-cancer, anti-microbial and the like) and by disease processes. (See, e.g., U.S. patent application Ser. No. 11/388,634).

"Conditions involving retinal degeneration" include, but are not limited to, laser-induced retinal damage and ophthalmic diseases, such as glaucoma, Retinitis pigmentosa, Usher syndrome, artery or vein occlusion, diabetic retinopathy, retrolental fibroplasias or retinopathy of prematurity (R.L.F./R.O.P.), retinoschisis, lattic degeneration, macular degeneration and ischemic optic neuropathy (see, e.g., U.S. Patent Appl. No. 60/776,329).

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder and attention deficit disorders) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV) (see also Benitez-King G. et al., *Curr Drug Targets CNS Neurol Disord* (2004) 3:515-33). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"Anxiety," "anxiety disorder," and "anxiety-related disorder" refer to psychiatric syndromes characterized by a subjective sense of unease, dread, or foreboding, e.g., panic disorder, generalized anxiety disorder, attention deficit disorder, attention deficit hyperactive disorder, obsessive-compulsive disorder, and stress disorders, e.g., acute and post-traumatic. Diagnostic criteria for these disorders are well known to those of skill in the art (see, e.g., *Harrison's Principles of Internal Medicine*, pp. 2486-2490 (Wilson et al., eds., 12th ed. 1991) and DSM IV).

An "autoimmune disorder" refers to an autoimmune disease such as multiple sclerosis, myasthenia gravis, Guillan-Barre syndrome (antiphospholipid syndrome), systemic lupus erytromatosis, Behcet's syndrome, Sjogrens syndrome, rheumatoid arthritis, Hashimoto's disease/hypothyroiditis, primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock (see, e.g., Schneider A. et al., J Biol. Chem. 2004, 279:55833-9).

"Motor dysfunctions" include muscle wasting and changes in gait, balance, and muscle strength. "Sensory dysfunctions" may be measured by changes in sense of smell, vision or hearing, or changes in deep tendon reflexes, vibratory sense, cutaneous sensation, or chronic or intermittent pain. Sometimes sensory dysfunctions are associated with disease, and can be experienced as pain or pins-and-needles, burning, crawling, or prickling sensations, e.g., in the feet and lower legs. In humans, both motor and sensory dysfunctions indicate effects in both the PNS and the CNS which may be caused by chemical (e.g., chemotherapeutics) or disease states.

The terms "polypeptide," "peptide" and "protein" are used interchangeably herein to refer to a polymer of amino acid residues. Generally, a peptide refers to a short polypeptide. The terms apply to amino acid polymers in which one or more amino acid residue is an analog or mimetic of a corresponding naturally occurring amino acid, as well as to naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. For the purposes of this application, amino acid analogs refers to compounds that have the same basic chemical structure as a naturally occurring amino acid, i.e., an α carbon that is bound to a hydrogen, a carboxyl group, an amino group, and an R group, e.g., alpha-aminoisobutyric acid, beta-aminoisobutyric acid, homoserine, norleucine, methionine sulfoxide, methionine methyl sulfonium. Such analogs have modified R groups (e.g., norleucine) or modified peptide backbones (beta-aminoisobutyric acid), but retain the same basic chemical structure as a naturally occurring amino acid.

The term "branched alkyl amino acid" refers to amino acids that have a non-linear carbon side-chain. Such branched alkyl amino acids can be one of the 20 standard amino acids (e.g., isoleucine, leucine, valine) or a non-standard amino acid (e.g., alpha-aminoisobutyric acid or beta-aminoisobutyric acid). For example, in some embodiments, proline can be substituted with alpha-aminoisobutyric acid (Gilead S. & Gazit E. (2004) *Angew Chem Int Ed Engl.*, 43:4041-4044), or another branched alkyl amino acid.

For the purposes of this application, "peptide analogs" and "peptide mimetics" refer to chemical compounds that have a structure that is different from the naturally-occurring chemical structure of a peptide, but that functions in a similar manner.

Amino acids can include those having non-naturally occurring D-chirality, as disclosed in WO 01/12654, which can improve oral availability and other drug like characteristics of the compound. In such embodiments, one or more, and potentially all of the amino acids of a peptide or peptide mimetic (e.g., NAP, NAP-IBA peptide) will have D-chirality. The therapeutic use of peptides can be enhanced by using D-amino acids to provide longer half life and duration of action. While many receptors exhibit a strong preference for L-amino acids, examples of D-peptides have been reported that have equivalent activity to the naturally occurring L-peptides, for example, pore-forming antibiotic peptides, beta amyloid peptide (no change in toxicity), and endogenous ligands for the CXCR4 receptor. In this regard, NAP and NAP-IBA peptides also retain activity in the D-amino acid form.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art (see, e.g., Creighton, *Proteins* (1984)). Such conservatively modified variants are in addition to and do not exclude polymorphic variants, interspecies homologs, and alleles of the invention.

In addition, certain protecting groups may be added to peptides according to the invention. The protecting group may be added to either the N-terminal or C-terminal end of the peptide, or both. As used herein, the term "protecting group" refers to a compound that renders a functional group unreactive, but is also removable so as to restore the functional group to its original state. Such protecting groups are well known to one of ordinary skill in the art and include compounds that are disclosed in "Protective Groups in Organic Synthesis", 4th edition, T. W. Greene and P. G. M. Wuts, John Wiley & Sons, New York, 2006. Examples of protecting groups include, but are not limited to: acetyl groups, amide groups, Fmoc (9-fluorenylmethyl carbamate, Boc, benzyloxy-carbonyl (Z), alloc (allyloxycarbonyl), and lithographic protecting groups. For example, an acetyl group and/or an amide group can be used to protect the peptide from degradation. The acetyl group is generally added to the C-terminus and the amide group is added at the N-terminus of a peptide.

The terms "isolated," "purified" or "biologically pure" refer to material that is substantially or essentially free from components that normally accompany it as found in its native state.

"An amount sufficient" or "an effective amount" or a "therapeutically effective amount" is that amount of a given polypeptide or peptide (e.g., NAP or NAP-IBA peptide) that exhibits the activity of interest or which provides either a subjective relief of a symptom(s) or an objectively identifiable improvement as noted by the clinician or other qualified observer. In therapeutic applications, the peptides of the invention are administered to a patient in an amount sufficient to reduce or eliminate symptoms. An amount adequate to accomplish this is defined as the "therapeutically effective dose." The dosing range varies with the peptide used, the route of administration and the potency of the particular peptide, as further set out below, and in CA Patent 2202496, U.S. Pat. No. 6,174,862 and U.S. Pat. No. 6,613,740.

The term "test compound" or "drug candidate" or "modulator" or grammatical equivalents as used herein describes any molecule, either naturally occurring or synthetic, e.g., protein, peptide (e.g., from about 5 to about 25 amino acids in length, from about 10 to 20 or 12 to 18 amino acids in length, e.g., 12, 15, or 18 amino acids in length), small organic molecule, polysaccharide, lipid, fatty acid, polynucleotide, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (or "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, less than about 2000 Daltons, between about 100 to about 1000 Daltons, or between about 200 to about 500 Daltons.

B. Introduction

NAP (NAPVSIPQ; SEQ ID NO:4) is an active neuroprotective peptide that has been shown to promote neurotrophism in vitro (Gozes et al., *CNS Drug Rev,* 11(4):353-368 (2005); Gozes and Spivak-Pohis, *Curr Alzheimer Res,* 3(3): 197-199 (2006)). NAP enhances neurodevelopment of newborn apolipoprotein E deficient mice subjected to hypoxia, suggesting neurotrophic activity in vivo (Gozes and Spivak-Pohis, supra (2006); Rotstein et al., *J Pharmacol Exp Ther,* (2006)). NAP was originally discovered to protect against beta amyloid (amino acids 25-35) toxicity in rat cerebral cortical neurons seeded on a bed of astrocytes, and these studies were extended to show that NAP protected against beta amyloid (25-35) in neuronal-enriched cultures (Bassan et al., supra (1999); Zemlyak et al., *Regul Pept,* 96:39-43 (2000)) and more recently to protection against the toxic beta amyloid peptide (1-42) which is found in the plaques in Alzheimer's disease (Gozes et al., *Curr Alzheimer Res,* (2007)).

The structural peptide characteristics required to inhibit or prevent the aggregation of the key component of the beta amyloid plaque in Alzheimer's disease the amyloid beta peptide (A-beta) include the following: (1) At least three hydrophobic amino acids in order to block the folding of the peptide/protein into beta sheet conformation; (2) One of the residues in the hydrophobic clusters preferably a beta sheet blocking amino acid, proline or asparagines; (3) The peptide should include polarized amino acids at one or both ends in order to increase its solubility; and (4) The peptide can be between 3 and 15 amino acids long, with a hydrophobic core in the middle consisting of 3-8 amino acids. NAP (NAPVSIPQ; SEQ ID NO:4) exhibits the required characteristics described above. There are polarized amino acids, glutamine (Q) and asparagine (N), at the ends of the molecule, which also possess the beta sheet blocker feature. Moreover, NAP has a 6-amino acid long hydrophobic core, including two prolines (P) that are described above as important in beta sheet blocking (Ashur-Fabian et al., *Peptides,* 24:1413-23 (2003)).

ADNP synthesis and secretion is induced by the neuroprotective vasoactive intestinal peptide (VIP), which, was originally associated with embryonic development and brain protection (Gozes et al., *Brain Res Dev Brain Res,* 99(2):167-75 (1997); Brenneman and Gozes, *J Clin Invest,* 97(10):22.99-307 (1996); Gozes and Brenneman, *J Mol Neurosci,* 7(4): 235-44 (1996); Gozes et al., *Molecular Chaperones and Cell Signalling,* 251-62 (2005)). The active core of ADNF-I, ADNF-9 (SALLRSIPA or "SAL"; SEQ ID NO:11), exhibits structural and functional similarities with NAP (Bassan et al., supra (1999); Gozes et al., *Ann N Y Acad Sci,* 897:125-35 (1999); Brenneman et al., *J Pharmacol Exp Ther,* 285(2): 61.9-27 (1998)). The function and properties of ADNF-9 (i.e., SAL) were recently reviewed (Gozes et al., *Molecular Chaperones and Cell Signalling,* 251-62 (2005)).

As it pertains to Alzheimer's disease, ADNF protects against beta amyloid peptide 25-35 toxicity (Brenneman and Gozes, *J Clin Invest,* 97(10):22.99-307 (1996)); and 1-42 (Hashimoto et al., *J Neurochem,* 90(3):549-58 (2004)). In addition, primary hippocampal neurons from presenilin 1

(PSI) mutant knock-in mice exhibiting increased production of amyloid beta-peptide 42/43 and increased vulnerability to excitotoxicity were protected by pretreatment with ADNF-9 (Guo et al., *Proc Nad Acad Sci USA*, 96:4125-30 (1999)).

The all D-amino acid analogs of NAP and ADNF-9 (D-NAP and D-SAL, respectively) have both shown neuroprotective activity (Brenneman et al., *J. Pharmacol Exp. Ther.* 309:1190-97 (2004)). D-SAL also protects against beta amyloid 1-42 toxicity (Gozes et al., *Curr Alzheimer Res*, (2007)).

As explained in the Examples, we have found that substitution of the two prolines in the NAPVSIPQ (SEQ ID NO:4) sequence with alpha-aminoisobutyric acid results in a peptide that is still highly neuroprotective. The results are especially surprising given the disclosure of Wilkemeyer et al., *Proc Natl Acad Sci USA*, 100(14):8543-8 (2003), which states that the SIP motif is essential for NAP neuroprotection. These findings provide additional lead compounds for drug development, e.g., with enhanced beta sheet breaker characteristics, and surprisingly demonstrate that the proline residues in the sequence NAPVSIPQ (SEQ ID NO:4) can be exchanged by non-conventional exchanges without a loss in neuroprotective activity. Accordingly, the invention provides peptides and peptides derived from NAP, including substitution of one or both of the proline residues, as well as related peptides.

C. Design and Synthesis of Peptides

Polypeptides and peptides comprising modifications of the core NAP peptide (NAPVSIPQ; SEQ ID NO:4) can be made, e.g., by systematically adding one amino acid at a time and screening the resulting peptide for biological activity, as described herein. For example, any one of the amino acids in the NAP core peptide may be substituted by a branched alkyl amino acid, e.g., alpha-aminoisobutyric acid. In addition, the contributions made by the side chains of various amino acid residues in such peptides can be probed via a systematic scan with a specified amino acid, e.g., Ala.

Polypeptides comprising non-standard amino acids can also be made. In some embodiments, at least one of the amino acids of the NAPVSIPQ (SEQ ID NO:4) peptide is a non-standard amino acid. In some embodiments, 2, 3, 4, 5, or more of the amino acids is a non-standard amino acid. Examples of non-standard amino acids are alpha-aminoisobutyric acid, N-methylated amino acids, amino acids with a D chiral center, aza-tryptophan, etc. A wide range of non-standard amino acids are commercially available, e.g., at Genzyme Pharmaceuticals (Cambridge, Mass.).

Polypeptide sequences, including those with non-standard amino acids, can be generated synthetically using commercially available peptide synthesizers to produce any desired polypeptide (see Merrifield, *Am. Chem. Soc.* 85:2149-2154 (1963); Stewart & Young, *Solid Phase Peptide Synthesis* (2nd ed. 1984)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids, or non-standard amino acids, in the sequence is a method for the chemical synthesis of the peptides of this invention. Techniques for solid phase synthesis are described by Barany & Merrifield, *Solid-Phase Peptide Synthesis*; pp. 3-284 in *The Peptides: Analysis, Synthesis, Biology*. Vol. 2: *Special Methods in Peptide Synthesis*, Part A.; Merrifield et al 1963; Stewart et al. 1984). NAP and NAP-IBA peptides can be synthesized using standard Fmoc protocols (Wellings & Atherton, *Methods Enzymol.* 289:44-67 (1997)).

In particular, peptides including alpha-aminoisobutyric acid can be generated using solid phase techniques. Alpha-aminoisobutyric acid is an amino acid with two methyl groups bound to C?. It is identical to alanine, but with an extra methyl group, and as a result is more sterically hindered. Alpha-aminoisobutyric acid can be incorporated into a peptide sequence according to standard techniques in the same manner as natural amino acids (see, e.g., Gilead & Gazit (2004) *Angew Chem Int Ed Engl.*, 43:4041-4044). Similarly, beta-aminoisobutyric acid, a non-standard amino acid with a 4-carbon chain backbone, can be incorporated according to standard techniques.

One of skill will recognize many ways of generating alterations in a nucleic acid sequence encoding a given peptide sequence. Polypeptide sequences can also be altered by changing the corresponding nucleic acid sequence and expressing the polypeptide. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other known techniques (see Giliman & Smith, *Gene* 8:81-97 (1979); Roberts et al., *Nature* 328:731-734 (1987)).

In addition to the foregoing techniques, the peptides for use in the invention can be prepared by recombinant DNA methodology. Generally, this involves creating a nucleic acid sequence that encodes the protein, placing the nucleic acid in an expression cassette under the control of a particular promoter, and expressing the protein in a host cell. Recombinantly engineered cells known to those of skill in the art include, but are not limited to, bacteria, yeast, plant, filamentous fungi, insect (especially employing baculoviral vectors) and mammalian cells.

The recombinant nucleic acids are operably linked to appropriate control sequences for expression in the selected host. For *E. coli*, exemplary control sequences include the T7, trp, or lambda promoters, a ribosome binding site and, optionally, a transcription termination signal. For eukaryotic cells, the control sequences can include a promoter and, optionally, an enhancer, e.g., derived from immunoglobulin genes, SV40, cytomegalovirus, etc., a polyadenylation sequence, and splice donor and acceptor sequences.

The plasmids of the invention can be transferred into the chosen host cell by methods such as, for example, the calcium chloride transformation method for *E. coli* and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant peptides can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology* Vol. 182: *Guide to Polypeptide Purification* (1990)). Optional additional steps include isolating the expressed protein to a higher degree, and, if required, cleaving or otherwise modifying the peptide, including optionally renaturing the protein.

One of skill can select a desired nucleic acid or polypeptide of the invention based upon the sequences provided and upon knowledge in the art regarding proteins generally. Knowledge regarding the nature of proteins and nucleic acids allows one of skill to select appropriate sequences with activity similar or equivalent to the nucleic acids and polypeptides disclosed herein.

After chemical synthesis, biological expression or purification, the peptide(s) may possess a conformation substantially different than the native conformations of the constituent peptides. In this case, it is helpful to denature and reduce the peptide and then to cause the peptide to re-fold into the preferred conformation. Methods of reducing and denaturing peptides and inducing re-folding are known to those of skill in the art (see Debinski et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body peptides in guanidine-DTE. The peptide is then refolded in a redox buffer containing oxidized glutathione and L-arginine.

Polypeptides or peptides can be evaluated by screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, hydrophobicity, susceptibility to proteolysis, or the tendency to aggregate can be assayed. More particularly, the small peptides of the present invention can be screened by employing suitable assays and animal models known to those skilled in the art.

One of skill will recognize that modifications can be made to the peptides without diminishing their biological activity. Some modifications may be made to facilitate the cloning, expression, or incorporation of the targeting molecule into a fusion peptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

D. Functional Assays of the Peptides of the Invention

One method to determine biological activity of a peptide of the invention (e.g., NAP-IBA peptide) is to assay its ability to protect neuronal cells from death. One such assay is performed using dissociated cerebral cortical cultures prepared as described (Brenneman & Gozes, *J. Clin. Invest.* 97:2299-2307 (1996)). The test paradigm consists of the addition of a test peptide to cultures that are co-treated with tetrodotoxin (TTX). TTX produces an apoptotic death in these cultures and, thus, is used as a model substance to demonstrate efficacy against this "programmed cell death" and all other means that produce this type of death mechanism. The duration of the test period is 5 days, and neurons are counted and identified by characteristic morphology and by confirmation with an immunocytochemical marker for neurons: e.g., neuron specific enolase.

In some aspects, the present invention provides a method for reducing neuronal cell death, the method comprising contacting neuronal cells with a peptide of the invention (e.g., NAP-IBA peptide) in an amount sufficient to reduce neuronal cell death. In a further aspect, the NAP-IBA peptide comprises at least one D-amino acid within its active core site, e.g., at the N-terminus and/or the C-terminus of the active core site.

Additional assays include screening for neuroprotective activity. Such activity can be tested in classical tissue culture models of neuronal stress and survival as described, e.g., in Divinski et al. (2006) and Gozes et al. (2005). These assays are known in the art and focus on the effect of test compounds on microtubule reorganization, neurite outgrowth, and protection from toxic factors.

Moreover, peptides that reduce neuronal cell death can be screened in vivo. The efficacy of peptides of the invention that can protect against learning and memory deficiencies associated with cholinergic blockade can be tested. For example, cholinergic blockade can be obtained in rats by administration of the cholinotoxin AF64A, and a NAP-IBA peptide can be administered intranasally, followed by water maze experiments (Gozes et al., *Proc. Natl. Acad. Sci. USA* 93:427-432 (1996)). Animals treated with efficacious peptides would show improvement in their learning and memory capacities compared to the control.

Furthermore, the efficacy of peptides that can protect or reduce neuronal cell death associated with Alzheimer's disease can be screened in vivo. For these experiments, apolipoprotein E (ApoE)-deficient homozygous mice can be used (Plump et al., *Cell* 71:343-353 (1992); Gordon et al., *Neuroscience Letters* 199:1-4 (1995); Gozes et al., *J. Neurobiol.* 33:329-342 (1997)).

In vivo assays to test neuroprotection in animal models are known in the art. Tests that measure effects of various test substances on motor activity include the rotorod and plantar tests, e.g., in rats. Olfaction capacity can be used to measure the effect of test substances on sensory activity. Such assays are described, e.g., in U.S. Patent Appl. No. 20060247168.

A well-established model for fetal alcohol syndrome can be used to test the efficacy of test compounds (Webster et al., *Neurobehav. Toxicol* 2:227-234 (1980)). This paradigm is a test for efficacy against severe oxidative stress produced from alcohol administration (Spong et al., 2001). This model allows for a rapid and relevant evaluation of agents efficacious against severe oxidative stress as well as fetal alcohol syndrome. To assess the protective effects of a test compound, the number of fetal demises can be determined.

Experiments to test the protective effect of an agent (e.g., NAP-IBA peptides) on retinal cells exposed to lasers, e.g., in conditions of laser surgery, are described in U.S. Prov. Appl. No. 60,776,329. In brief, rats were exposed to laser photocoagulation and immediately treated either systemically or intravitreously with a protective compound. The animals were sacrificed and retinal tissue sections were observed for histological and morphological abnormalities.

E. Therapeutic Uses for the Peptides of the Invention

The peptides of the invention (e.g., NAP-IBA peptides) can be used in the treatment of neurological disorders and for the prevention of neuronal cell death. For example, the peptides of the invention can be used to prevent the death of neuronal cells including, but not limited to, spinal cord neurons, hippocampal neurons, cerebral cortical neurons and cholinergic neurons. More particularly, the peptides of the present invention can be used in the prevention of cell death associated with (1) gp120, the envelope protein from HIV; (2) N-methyl-D-aspartic acid (excito-toxicity); (3) tetrodotoxin (blockage of electrical activity); and (4) β-amyloid peptide, a substance related to neuronal degeneration in Alzheimer's disease.

As such, the peptides of the invention can be used to reduce gp120-induced neuronal cell death by administering an effective amount of a peptide of the present invention to a patient infected with the HIV virus. The peptides of the invention can also be used to reduce neuronal cell death associated with excito-toxicity induced by N-methyl-D-aspartate stimulation, the method comprising contacting neuronal cells with a peptide of the invention in an amount sufficient to prevent neuronal cell death. The peptides of the invention can also be used to reduce cell death induced by the ?-amyloid peptide in a patient afflicted or impaired with Alzheimer's disease, the method comprising administering to the patient a peptide of the invention in an amount sufficient to prevent neuronal cell death. The peptides can also be used to alleviate learning impairment produced by cholinergic blockage in a patient afflicted or impaired with Alzheimer's disease. For example, the peptides of the invention can be used to improve short-term and/or reference memory in Alzheimer's patients.

The peptides of the present invention can be used in a similar manner to prevent neuronal cell death associated with a number of other neurological diseases and deficiencies. Pathologies that would benefit from therapeutic and diagnostic applications of this invention include conditions (diseases and insults) leading to neuronal cell death and/or sub-lethal neuronal pathology including, for example, the following: diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity; diseases affecting sensory neurons such as Friedreich's ataxia, diabetes, peripheral neuropathy, retinal neuronal degeneration; diseases of limbic and cortical systems such as cerebral amyloidosis, Pick's atrophy, Retts syndrome; neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration; pathologies associated with developmental retardation, learning impairments, and Down's syndrome; oxidative stress-induced neuronal death; pathologies arising with aging and chronic alcohol or drug abuse (e.g., for alcoholism, the degeneration of neurons in locus coeruleus, cerebellum, cholinergic basal forebrain and for aging, degeneration of cerebellar neurons and cortical neurons leading to cognitive and motor impairments); pathologies arising with chronic amphetamine abuse; pathological changes resulting from focal trauma such as stroke, focal ischemia, vascular insufficiency, hypoxic-ischemic encephalopathy, hyperglycemia, hypoglycemia, closed head trauma, or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor, peripheral neuropathies resulting from, e.g., chemotherapy treatments, and retinal damage from laser eye treatments).

F. Drug Discovery

Peptides of the invention that reduce neuronal cell death can be validated using the various methods described above, or those in WO98/35042 and U.S. Pat. No. 6,613,740. One of ordinary skill in the art can identify other biologically active peptides comprising at least one non-standard amino acid within their active core sites. For example, Brenneman et al., *Nature* 335:639-642 (1988), and Dibbern et al., *J. Clin. Invest.* 99:2837-2841 (1997), teach assays that can be used to screen NAP-IBA peptides that are capable of reducing neuronal cell death associated with envelope protein (gp120) from HIV. Also, Brenneman et al., *Dev. Brain Res.* 51:63-68 (1990), and Brenneman & Gozes, *J. Clin. Invest.* 97:2299-2307 (1996), teach assays that can be used to screen the peptides of the invention which are capable of reducing neuronal cell death associated with excito-toxicity induced by stimulation by N-methyl-D-aspartate.

High throughput screening methods involving providing a combinatorial chemical or peptide library containing a large number of potential therapeutic compounds (e.g., potential NAP-IBA peptides) can be used. Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics. Libraries available for screening for small active molecules include the Available Chemical Directory (ACD, 278,000 compounds), ACD screening library (>1,000,000 compounds), CRC Combined Chemical Dictionary (~350,000 compounds) Anisex (115,000 compounds) Maybridge (62,000 compounds) Derwent and NCI libraries.

G. Pharmaceutical Compositions and Administration

The pharmaceutical compositions of the present invention are suitable for use in a variety of drug delivery systems. Peptides and peptides that have the ability to cross the blood brain barrier can be administered, e.g., systemically, nasally, by dermal patch etc., using methods known to those of skill in the art. NAP-IBA peptides can also be orally administered. Larger peptides that do not have the ability to cross the blood brain barrier can be administered to the mammalian brain via intracerebroventricular (ICV) injection or via a cannula using techniques well known to those of skill in the art (see, e.g., Motta & Martini, *Proc. Soc. Exp. Biol. Med.* 168:62-64 (1981); Peterson et al., *Biochem. PharamacoL* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)).

Suitable formulations for use in the present invention are found in Remington's *Pharmaceutical Sciences* (17th ed. 1985)). For a brief review of methods for drug delivery, see Langer, *Science* 249:1527-1533 (1990). Suitable dose ranges are described in the examples provided herein, as well as in WO9611948.

As such, the present invention provides for therapeutic compositions or medicaments comprising one or more of the polypeptides described hereinabove in combination with a pharmaceutically acceptable excipient, wherein the amount of polypeptide is sufficient to provide a therapeutic effect.

In a therapeutic application, the polypeptides of the present invention are embodied in pharmaceutical compositions intended for administration by any effective means, including parenteral, topical, oral, nasal, pulmonary (e.g. by inhalation) or local administration. Nasal pumps, eye drops, and topical patches can be used.

The invention provides compositions for parenteral administration that comprise a solution of polypeptide, as described above, dissolved or suspended in an acceptable carrier, such as an aqueous carrier. Parenteral administration can comprise, e.g., intravenous, subcutaneous, intradermal, intramuscular, or intranasal administration. A variety of aqueous carriers may be used including, for example, water, buffered water, 0.4% saline, 0.3% glycine, hyaluronic acid and the like. These compositions may be sterilized by conventional, well known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride potassium chloride, calcium chloride, sorbitan monolaurate, triethanolamine oleate, etc.

For solid compositions, conventional nontoxic solid carriers may be used that include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides are preferably supplied in finely divided form along with a surfactant and propellant. Accordingly, in some embodiments, the pharmaceutical composition comprises a surfactant such as a lipophilic moiety to improve penetration or activity. Lipophilic moieties are known in the art and described, e.g., in U.S. Pat. No. 5,998,368. The surfactant must be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., *J Mol Neurosci.* 19:167-70 (2002)).

In therapeutic applications, the polypeptides of the invention are administered to a patient in an amount sufficient to reduce or eliminate symptoms of neurodegenerative disorders and cognitive deficits. An amount adequate to accomplish this is defined as "therapeutically effective dose." Amounts effective for this use will depend on, for example, the particular polypeptide employed, the type of disease or disorder to be prevented, the manner of administration, the weight and general state of health of the patient, and the judgment of the prescribing physician.

For example, an amount of a peptide falling within the range of a 100 ng to 10 mg dose given intranasally once a day would be a therapeutically effective amount. Alternatively, dosages may be outside of this range, or on a different schedule. For example, dosages can range from 0.0001 mg/kg to 10,000 mg/kg, and can be about 0.001 mg/kg, 0.1 mg/kg, 1 mg/kg, 5 mg/kg, 50 mg/kg or 500 mg/kg per dose. Doses may be administered hourly, every 4, 6 or 12 hours, with meals, daily, every 2, 3, 4, 5, 6, or 7 days, weekly, every 2, 3, 4 weeks, monthly or every 2, 3 or 4 months, or any combination thereof. The duration of dosing may be single (acute) dosing, or over the course of days, weeks, months, or years, depending on the condition to be treated. Those skilled in the art can determine the suitable dosage depending on the particular circumstances, and may rely on preliminary data reported in Gozes et al., 2000, Gozes et al., 2002, Bassan et al. 1999; Zemlyak et al., *Regul. Pept.* 96:39-43 (2000); Brenneman et al., *Biochem. Soc. Trans.* 28: 452-455 (2000); *Erratum Biochem Soc. Trans.* 28:983; Wilkemeyer et al. *Proc. Natl. Acad. Sci. USA* 100:8543-8548 (2003)).

H. Bioavailability

Cellular Bioavailability

Fluorescein-labeled NAP was detected in the intracellular milieu of neurons and astrocytes. In astrocytes, labeled NAP was found even when incubated at 4° C. and in conditions of low pH, indicating membrane permeability. Comparison of NAP with known membrane permeating peptides has shown that NAP possesses a membrane permeation structure (Divinski et al., *J Biol Chem,* 279(27):28531-28538 (2004)). Both NAP and ADNF-9 (SAL) are active in their all D-amino acid conformation, indicating that these peptides are mechanistically nonchiral (Brenneman et al., supra (2004)). NAP interacts with intracellular tubulin to enhance microtubule polymerization and provide cellular protection. However, NAP interacts with specific tubulin subunits and does not provide protection to all cells. Indeed, NAP did not protect fibroblast-like cells, but did protect neuronal-like cells against oxidative stress (Divinski et al., *J Neurochem,* 98(3):973-84 (2006)). These results are in line with our original studies suggesting that NAP interacts selectively to brain specific tubulin subunits that are associated with multiple tubulin functions (Gozes and Littauer, *Nature,* 276(5686):411-3 (1978); Gozes and Sweadner, *Nature,* 294(5840):477-80 (1981); Gozes and Barnstable, *Proc Natl Acad Sci USA,* 79(8):2579-83 (1982)).

Brain Bioavailability and Clinical Development

Figure 1:
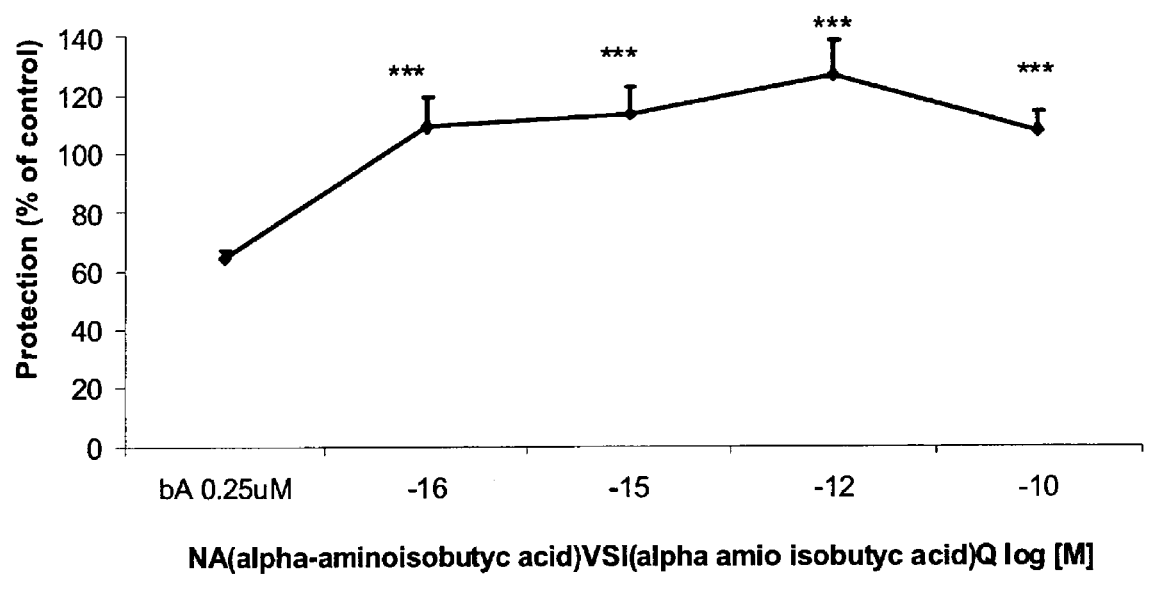

The pharmacodynamic compartment for NAP and NAP-IBA peptides is the brain or the central nervous system (CNS). When NAP or NAP-IBA peptides are administered, the composition must be able to reach the CNS at pharmacologically active concentrations. As shown in FIGS. 1 and 2, alpha-aminoisobutyric NAP and NAP exhibit an in vitro potency of $\sim 10^{-16}$-$10^{-15}$ M. Preclinical and Phase I clinical experiments demonstrated that intranasal administration of NAP to rats, dogs or humans results in measurable plasma levels (Gozes et al., *CNS Drug Rev,* 11(4):353-68 (2005)). After intranasal administration of [3H]-NAP to rats, radioactivity was detected in the blood and various organs of the body (Gozes et al., *J Pharmacol Exp Ther,* 293(3):1091-8 (2000)). Intact peptide was identified in the rat cortex 30 minutes and 60 minutes following intranasal administration. In the permanent middle cerebral artery occlusion (PMCAO) rat model, intravenous administration of radioactive NAP resulted in measurable levels in the cerebellum and cortex 15 minutes after injection and was maintained for at least 30 minutes in the ischemic tissue (Leker R. R. et al., *Stroke,* 33(4):1085-92 (2002)). Liquid chromatography mass spectrometry assays in rats and dogs corroborated and extended these results. Recent data from a pharmacokinetic study in rats suggested a correlation between plasma and cerebrospinal fluid (CSF) levels of NAP administered by intravenous injection. Following intranasal administration in the rat, NAP exhibited rapid appearance in plasma and the kinetics of appearance in CSF (Tmax) appears to lag plasma Tmax (Gozes et al., *CNS Drug Rev,* 11(4):353-368 (2005); Morimoto et al., *Drug Metabolism*

Reviews, 38 (suppl 2):213-14 (2006)). Therefore, it is likely that access to the brain is via the circulation for both intravenous and intranasal routes.

EXAMPLES

Example 1

NAP-IBA Peptides Confer Neuroprotection from Beta Amyloid Peptides

Materials and Methods

Peptides

The octapeptide NAPVSIPQ (SEQ ID NO:4) was synthesized to include alpha-aminoisobutyric acid rather than proline (as per synthesis described in (Gilead and Gazit, *Angew Chem Int Ed Engl*, 43(31):4041-4044 (2004)). The resulting peptide is described herein as SEQ ID NO:1.

All peptides were dissolved in distilled sterile water to a concentration of 1 mM and then diluted in water in 1:10 steps up to the required concentration. The beta-amyloid peptide (1-42) was obtained from American Peptides, Calif., USA.

Cell Cultures and Neuronal Survival

Cerebral cortical cultures derived from newborn rats were used for neuron survival assays. For mixed neuroglial cultures, neurons 300,000 cells/35 mm dish were seeded on 8-day-old astrocytes prepared as described (Bassan et al., supra (1999); Brenneman et al., supra (2004)). Cells were allowed to grow for one week at 37° C. 10% $CO_2$ before experiments were performed. Four days after neuronal plating, cultures were given their respective treatment and assayed for neuronal survival after an additional 5 day incubation period.

Neuronal Cell Counts

The culture medium was removed and cells were washed twice with phosphate buffered saline (PBS). 1.5 ml of 3% glutaraldehyde (Fluka Biochemika, Steinheim, Germany) in 0.1 M cacodylic acid pH 7.2 (Fluka Biochemika, Steinheim, Germany) was added for two hours. The cells were then washed with PBS and 2 ml of 0.15 M cacodylic acid pH 7.2 was added. Neuronal identity was established by morphological criteria using an Olympus CK2 light microscope (Olympus, Japan) with a X40 lens. Fifty fields were counted in each dish (Zemlyak et al., supra (2000)).

Results

The number of surviving neurons was assessed in cerebral cortical cultures derived from newborn rats using the beta-amyloid peptide (1-42), an Alzheimer's disease-associated toxin, at 2.5 µM. Alpha-aminoisobutric NAP was used at the following concentrations: $10^{-16}$M, $10^{-15}$M, $10^{-12}$M, $10^{-10}$M. The peptide protected against neurotoxicity associated with the beta-amyloid peptide 1-42 (p<0.001). Maximal protection was observed at concentrations of $10^{-15}$M-$10^{-10}$M (FIG. 1). Cell counts totaled>100% of control, because the treatment prevents neuronal cell death that occurred naturally in the cultures (10-20%), as observed before (Bassan et al., supra (1999)). Comparison with unmodified NAP surprisingly indicates increased activity in the modified novel NAP analogue (compare FIG. 2). This is an unexpected finding in view of previous reports that describe the SIP motif as essential for NAP neuroprotection (Wilkemeyer et al., *Proc Natl Acad Sci USA*, 100(14):8543-8 (2003)).

Example 2

Effect of NAP and NAP Alpha-Aminoisobutyric Acid on tau Pathological Aggregation Leading to Neurofibrillary Tangle Formation VQIVYK Aggregation Tau is a highly soluble protein. The unfolded tau protein lacks a defined 3D structure. Its main role is stabilization of microtubules in neuronal axons. Tau protein contains three or four microtubule binding repeats. $^{306}$VQIVYK$^{311}$ (SEQ ID NO:10) is a peptide derived from the beginning of the third microtubule binding repeat of tau (which is present in all tau variants). This sequence was found to be important for the aggregation of tau into paired helical filaments (PHFs), which aggregate to make the tangles found in Alzheimer's disease and related disorders. See, e.g., Friedhoff et al., *Biochemistry* 1998, 37:10223-10230; Perez et al., J. of Neurochemistry, 2007, 103:1447-1460; and von Bergen et al., *Pro. Nat. Aca. Sci. USA* 2000, 97:5129-5134. Inhibition of tau aggregation therefore provides a means for treating diseases and conditions where tau aggregation is involved.

The aim of this study was to compare NAP alpha-aminoisobutyric acid (where the prolines in NAPVSIPQ (SEQ ID NO:4) were substituted with alpha-aminoisobutyric acid) with NAPVSIPQ (SEQ ID NO:4) containing prolines in an in vitro tau-like aggregation assay.

In the presence of polyglutamic acid (or heparin), VQIVYK (SEQ ID NO:10) aggregates which can be further detected by Thioflavin S (excitation 485 nm and emission 535) with emission intensity greatly increasing.

First, different concentrations of polyglutamic acid (0, 100 µM, 250 µM, and 400 µM) VQIVYK (SEQ ID NO:10) and either sodium acetate ($NH_4Ac$) 50 mM pH 6.5 or MOPS 20 mM pH 6.5 and Thioflavin S 5 µM were mixed together and incubated at room temperature. The extent of aggregation was read at excitation 485 nm and emission 535 nm using the infinite 200 system with the Magellan program.

Figure 3:
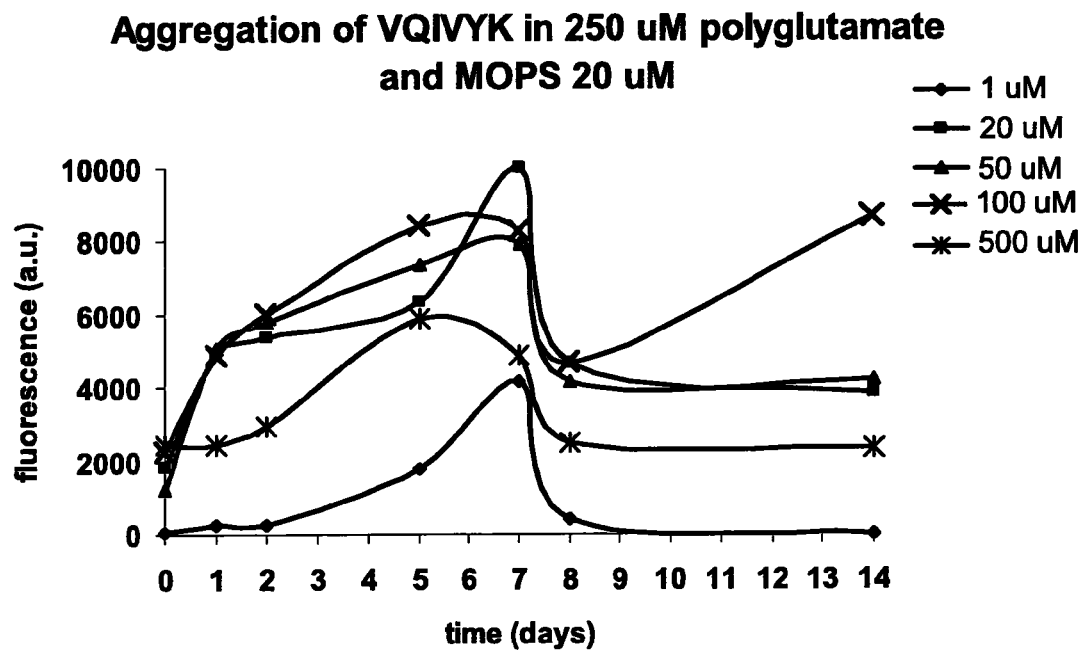
FIG. 3 is a time course of VQIVYK (SEQ ID NO:10) aggregation (increasing concentrations from 1-500 μM) in the presence of 250 μM polyglutamate and MOPS 20 mM, pH 6.5.

Optimal aggregation conditions were found to be at 7 days with 100 µM VQIVYK (SEQ ID NO:10), 250 µM polyglutamate and 20 mM MOPS pH 6.5. See FIG. 3.

The peptides were added at a range of concentrations ($10^{-17}$-$10^{-9}$ M) and the extent of aggregation of 100 µM VQIVYK (SEQ ID NO:10) was tested in the presence of polyglutamate 250 µM in MOPS 20 µM, pH 6.5 for 7 days.

In order to avoid reading self peptide aggregation as VQIVYK aggregation, for each peptide concentration, the fluorescence of the peptide solution without VQIVYK was subtracted from the fluorescence of each peptide concentration containing VQIVYK.

Figure 4:
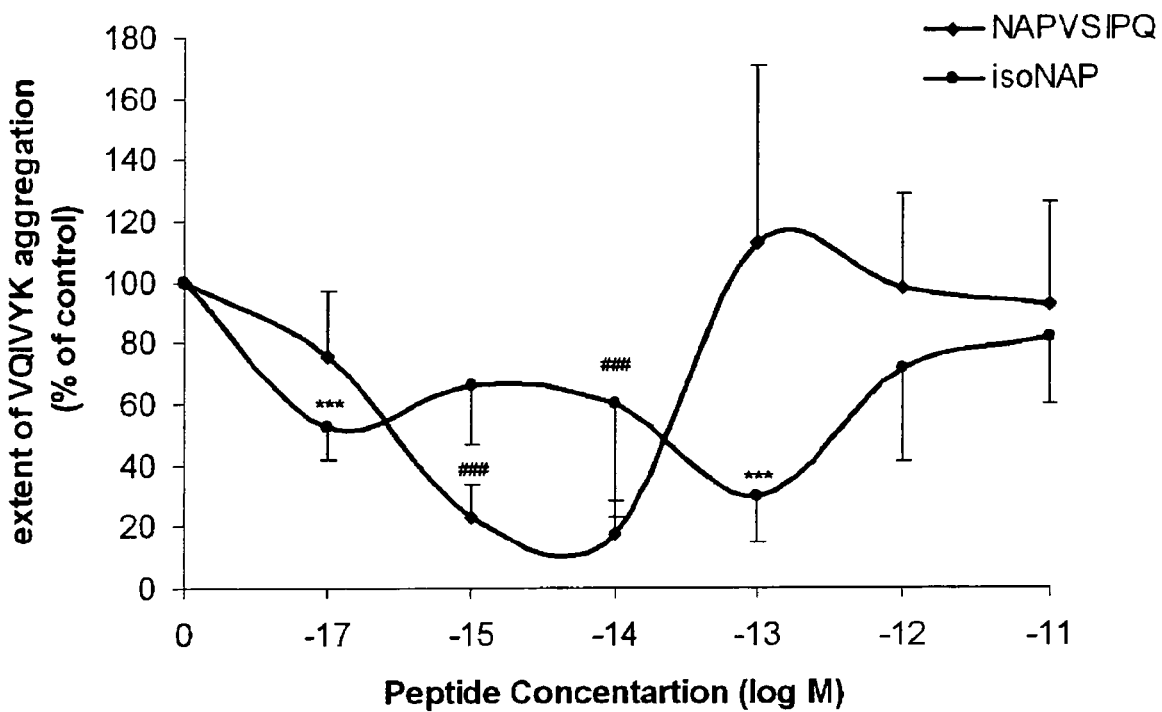
FIG. 4 is a graphic representation of three independent experiments performed in quadruplicates. IsoNAP (the NAP (NAPVSIPQ; SEQ ID NO:4) alpha-aminoisobutyric acid analogue) is more effective than NAP in inhibiting tau aggregation at $10^{-17}$M of VQIVYK (SEQ ID NO:10) peptide and at $10^{-13}$M of VQIVYK (SEQ ID NO:10) peptide. ###p<0.0005 NAP vs. control; ***=p<0.0005 isoNAP vs. control.
Figure 5:
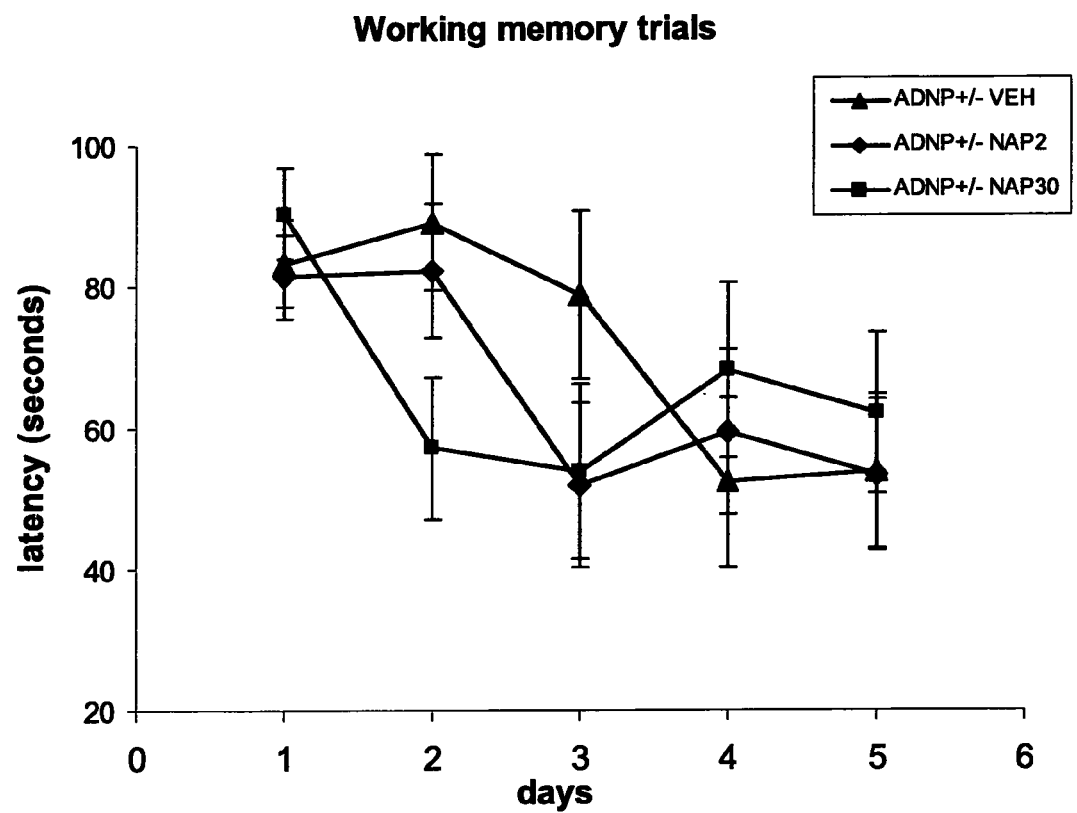
FIG. 5: On testing 3, Iso-NAP-treated (2 μg/5 μl/mouse/day) mice (termed NAP2 in the graph) performed better than controls (ADNP+/−). The 30 μg/5 μl/mouse/day was better than control on testing days 2 and 3 (termed NAP30 on the graph). The statistical test was per independent samples, 1-tailed t-test showing P<0.05 on day 2 of testing for the 30 μg IsoNAP/5 μl/mouse/day compared to vehicle treated mice, this was apparently maintained also on the third day of testing, P<0.07 and was also found at the 2 μg IsoNAP/5 μl/mouse/day, on the third day of testing, P<0.05.
Figure 6:
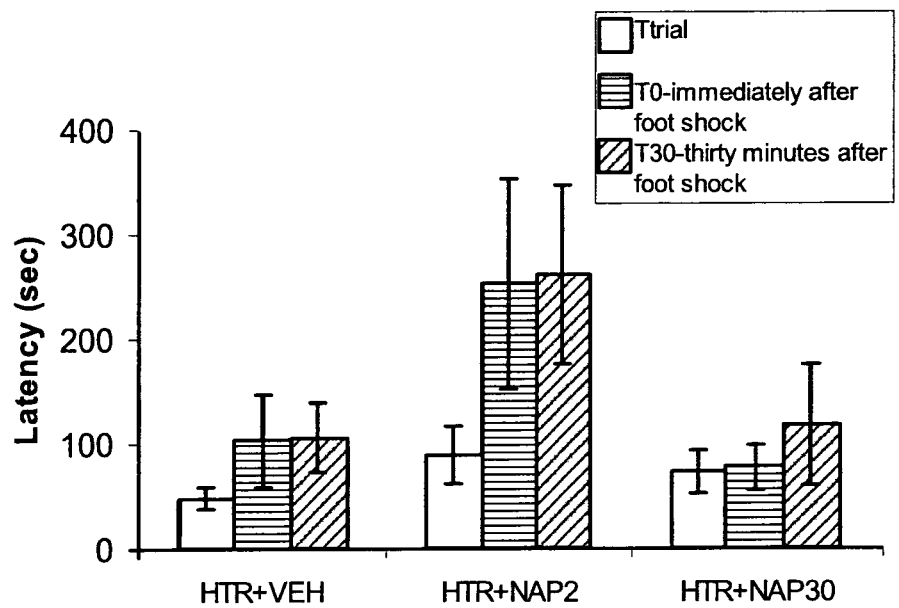
FIG. 6 demonstrates the mean latency to enter the dark room for each group in T-trial (acquisition trial), T0 (immediately after foot shock) and T30 (30 min after foot shock). The heterozygous mice treated with IsoNAP 2 μg/mice (NAP2) remembered the foot shock and on T0 and on T30 they entered the dark room significantly slower than on the T-trial (P<0.05). The statistical test was paired samples, 1-tailed t-test for the T0, and 2-tailed t-test for the 30 min. The control group VEH as well as the (30 μg/mice) NAP30 group entered the dark room faster than the NAP2 group.

IsoNAP (the NAP alpha-aminoisobutyric acid analogue) seems to be superior to NAP in terms of inhibition of tau aggregation at $10^{-17}$M of VQIVYK (SEQ ID NO:10) peptide (isoNAP is more potent) and at $10^{-13}$M of VQIVYK (SEQ ID NO:10) peptide (isoNAP remains effective whereas the effect of NAP seems to diminish). See FIG. 4. As such, this assay shows that isoNAP and NAP are both effective for preventing tau aggregation and therefore for treating tauopathies. They may be administered alone or in combination with each other.

Example 3

Neuroprotection In Vivo

Aims of the Study

Evaluate the effect of chronic two-week-daily treatments with Iso-NAP on cognitive performance of the ADNP heterozygous mice.

Materials and Methods

Generation of ADNP$^{+/-}$ Male Mice:

The heterozygous ADNP mice were generated as before (Pinhasov et al., *Brain Res. Dev. Brain Res.* 2003, 144:83-90; and Vulih-Shultzman et al., *J Pharmacol Exp Ther.* 2007, 323(2):438-49). To avoid any variability in results associated with the estrous cycle in females, only ADNP$^{+/-}$ male mice are use for behavioral experiments.

Iso-NAP Administration:

Iso-NAP (NAXaaVSIXaaQ; SEQ ID NO:1) was dissolved in a vehicle solution, in which each milliliter included 7.5 mg of NaCl, 1.7 mg of citric acid monohydrate, 3 mg of disodium phosphate dihydrate, and 0.2 mg of benzalkonium chloride solution (50%). Iso-NAP or vehicle solution (DD) was administered to mice handheld in a semi-supine position with nostrils facing the investigator. A pipette tip was used to administer 2.5 µl/each nostril. The mouse was handheld until the solution is entirely absorbed. Nasal Iso-NAP application was performed daily, once a day, for 2 weeks for the Morris water maze test. In the 2nd week, Iso-NAP was applied 1 h before the daily test (see below), which was conducted for 5 consecutive days. In the passive avoidance test, all mice were treated for a total of 7 days, on the 7th day of treatment the test began. Iso-NAP was applied 1 h before the test.

Morris Water Maze Test:

Richard G. Morris developed the Morris water maze task in 1984 (*J. Neurosci. Methods* 11:47-60). Since then this test has become one of the "gold standards" of behavioral neuroscience and it is widely used to study spatial learning and memory (i.e., acquisition and retention).

The mouse is placed in a pool of water that is colored opaque with powdered non-fat milk, where it must swim to a hidden escape platform. The position of the platform is altered between days but remains constant within each day. Because it is in opaque water, the mouse cannot see the platform, and cannot rely on scent to find the escape route. As the mouse becomes more familiar with the task, it is able to find the platform more quickly.

Test Conditions:

Pool diameter—140 cm, Platform—clear plaxiglass, 12 cm in diameter, 2 cm below the surface of the water, Water temperature—22-23° C., Room temperature—26-28° C.

Experimental Procedure:

Mice are treated with Iso-NAP/vehicle and then habituated for 1 hour in the experimental room. The test mouse is placed on the platform for 30 seconds followed by 2 sequential trials with a cut-off of 90 seconds and an Intra Experimental Interval (IEI) of 30 seconds in which it stays on the platform. (If the mouse doesn't reach the platform in 90 seconds, the handler guides it to the platform). The time requires to reach the platform in each trial is measured. The first daily trial aimed to assess the mouse's learning ability (reference memory) (Brandeis et al., *Int. J. Neurosci.* 1989, 48:26-69). Although the mice are naive about the platform's location on the first daily trials, the latency to find the platform declines over days, as it learns the concept that a platform is located somewhere within the pool (i.e., reference memory). The second daily trial is aimed to assess the mouse's short-term memory (working memory) (Brandeis et al., *Int. J. Neurosci.* 1989, 48:26-69). On any given day, once the platform is located, the mouse must maintain that memory over the short term, based on the platform's position during the immediately preceding trial (i.e., working memory). After all mice complete the fifth day trials, each mouse has to perform one probe trial, in which the platform is removed from the pool. The probe trial is performed to verify the mouse's understanding of the platform location, and observe the strategy that the mouse follows when it discovers that the platform is not there. The handler releases the mouse at the same place at the pool as on the prior trial. Recording the time the mouse spent in the quarter in which the platform was situated on the prior trial. A visual ability test is also conducted on the last day of the trial, to verify that all mice are capable of seeing.

Passive Avoidance Test:

The passive avoidance task is a fear-motivated avoidance task based on the mouse conflict between avoiding the light stimulus and approaching the dark chamber in which a painful shock is given. The mouse learns to refrain from stepping through a door to an apparently safer but previously punished dark compartment. The latency to refrain from crossing into the punished compartment serves as an index of the ability to avoid, and allows memory to be assessed (Johns Hopkins University, Department of Psychological and Brain Sciences, website: nbc.jhu.edu/protocols/PassiveAvoidanceProtocol.aspx).

Mice are tested in a step-through passive avoidance task. The apparatus consists of a light, white compartment and a dark, black compartment separated by a guillotine door.

The experiment is carried out for three days. The first day is habituation day, in which the apparatus is introduced to the tested mice. The mouse is placed in the light compartment and the door is opened 1 min later. The time to enter the dark compartment is recorded. Once all four paws are in the dark compartment, the door is closed and no foot shock is given. On the second day, during the acquisition trial (T-trial), the mouse is placed in the light compartment. The door is opened after 30 seconds, and the time it takes the mouse to enter the dark chamber is recorded. After the mouse enters, the door is closed behind it and two foot shocks of 0.7 mA each, 2 seconds each are given (Boura et al., *Behav. Brain Res.* 2008, 193:174-182). After 30 seconds in the dark compartment, the mouse is removed and placed in the illuminated chamber again. After 30 seconds (T0), the door is opened and the latency to enter the dark chamber is recorded. Cut-off time is ten minutes. The mice are tested again after 30 minutes (T30) and 140 minutes (T140). On the third day, the mice are tested again in order to examine 24 h retention. The mouse is always placed against the wall opposite to the dark compartment, so it has to cross the white compartment to reach the guillotine door.

Results

Morris Water Maze Results:

The MWM test included two experimental groups: ADNP heterozygous male mice (ADNP$^{+/-}$), 3-4 month old, treated by intranasal administration of Iso-NAP 2 µg/5 µl/mouse/day (n=10) or 30 µg/5 µl/mouse/day (n=10), and one control group: Heterozygous male mice treated by intranasal administration of vehicle (5 µl/mouse/day) (n=10)). The results of the working memory are shown.

Passive Avoidance Results:

The passive avoidance test included two experiment groups: ADNP heterozygous male mice 6-7 month old treated by intranasal administration of Iso-NAP 2 µg/5 µl/mouse/day (n=9) or 30 µg/5 µl/mouse/day (n=10), and one control group: heterozygous male mice treated by intranasal administration of vehicle (SW/mouse/day) (n=9).

CONCLUSION

At 2 μg/mice—IsoNAP seems to affect positively learning and memory, and the higher dose seems to affect the spatial memory.

The examples set out above are intended to be exemplary of the effects of the invention, and are not intended to limit the embodiments or scope of the invention contemplated by the claims set out below. Other variants of the invention will be readily apparent to one of ordinary skill in the art and are encompassed by the appended claims. All publications, databases, Genbank sequences, GO terms, patents, and patent applications cited in this specification are incorporated by reference in their entireties, as if each individual publication or patent application were specifically and individually indicated to be incorporated by reference.

This application is related to PCT WO 01/92333; U.S. Ser. No. 07/871,973 filed Apr. 22, 1992, now U.S. Pat. No. 5,767,240; U.S. Ser. No. 08/342, 297, filed Oct. 17, 1994 (published as WO96/11948), now U.S. Pat. No. 6,174,862; U.S. Ser. No. 60/037,404, filed Feb. 7, 1997 (published as WO98/35042); U.S. Ser. No. 09/187,330, filed Nov. 11, 1998 (published as WO00/27875); U.S. Ser. No. 09/267,511, filed Mar. 12, 1999 (published as WO00/53217); U.S. Pat. No. 6,613,740, U.S. Ser. No. 60/149,956, filed Aug. 18, 1999 (published as WO01/12654); U.S. Ser. No. 60/208,944, filed May 31, 2000 and U.S. Ser. No. 60/267,805, filed Feb. 8, 2001 (both published as US20040048801).

The invention claimed is:

1. A NAP peptide, wherein the NAP peptide has the formula $(R^1)_a$-$(R^2)$-$(R^3)_b$ in which
    $R^2$ is a member selected from the group consisting of: NAXaaVSIXaaQ (SEQ ID NO:36), NAXaaVSIPQ (SEQ ID NO:39), and NAPVSIXaaQ (SEQ ID NO:40), wherein Xaa is a branched alkyl amino acid;
    $R^1$ is an amino acid sequence independently selected from the group consisting of Gly-Gly-, Leu-Gly-Gly-, Leu-Gly-Leu-Gly-Gly- (SEQ ID NO:9), and Ser-Val-Ala-Leu-Gly-Leu-Gly-Gly-(SEQ ID NO:41);
    $R^3$ is -Gln-Ser; and
    a and b are independently selected and are equal to zero or one; and wherein the NAP peptide has neuroprotective activity.

2. The NAP peptide of claim 1, wherein the branched amino acid is selected from the group consisting of: alpha-aminoisobutyric acid, beta-aminoisobutyric acid, leucine, isoleucine, and valine.

3. The NAP peptide of claim 2, wherein the branched amino acid is alpha-aminoisobutyric acid.

4. The NAP peptide of claim 1, wherein $R^2$ is NAXaaVSIXaaQ (SEQ ID NO:36).

5. The NAP peptide of claim 1, wherein a and b are both zero.

6. The NAP peptide of claim 1, which has consists of the amino acid sequence of SEQ ID NO:5, SEQ ID NO:6, SEQ ID NO:7, or SEQ ID NO:8.

7. A pharmaceutical composition comprising the NAP peptide of claim 1.

8. The composition of claim 7, further comprising the peptide consisting of the amino acid sequence of SEQ ID NO:4.

* * * * *

```
SEQUENCE LISTING

<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: synthetic substituted NAP peptide (NAP-IBA,
      IsoNAP)
<220> FEATURE:
<221> NAME/KEY: MOD_RES
<222> LOCATION: (3)...(7)
<223> OTHER INFORMATION: Xaa = alpha-aminoisobutyric acid (IBA)

<400> SEQUENCE: 1

Asn Ala Xaa Val Ser Ile Xaa Gln
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic substituted NAP peptide (NAP-IBA)
<220> FEATURE:
<221> NAME/KEY: MOD_RES
<222> LOCATION: (3)...(3)
<223> OTHER INFORMATION: Xaa = alpha-aminoisobutyric acid (IBA)

<400> SEQUENCE: 2

Asn Ala Xaa Val Ser Ile Pro Gln
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic substituted NAP peptide (NAP-IBA)
<220> FEATURE:
<221> NAME/KEY: MOD_RES
<222> LOCATION: (7)...(7)
<223> OTHER INFORMATION: Xaa = alpha-aminoisobutyric acid (IBA)

<400> SEQUENCE: 3

Asn Ala Pro Val Ser Ile Xaa Gln
1               5

<210> SEQ ID NO 4
<211> LENGTH: 8
<212> TYPE: PRT
<213> ORGANISM: Artificial Sequence
<220> FEATURE:
```

```
<223> OTHER INFORMATION: synthetic activity-dependent neuroprotective
      protein (ADNP) NAP peptide, active core site, core peptide

<400> SEQUENCE: 4

Asn Ala Pro Val Ser Ile Pro Gln
 1               5

<210> SEQ ID NO 5
<211> LENGTH: 10
<212> TYPE: PRT
<213> ORGANISM: Artificial Sequence
<220> FEATURE:
<223> OTHER INFORMATION: synthetic substituted NAP peptide (NAP-IBA)
<220> FEATURE:
<221> NAME/KEY: MOD_RES
<222> LOCATION: (5)...(9)
<223> OTHER INFORMATION: Xaa = alpha-aminoisobutyric acid (IBA)

<400> SEQUENCE: 5

Gly Gly Asn Ala Xaa Val Ser Ile Xaa Gln
 1               5                   10

<210> SEQ ID NO 6
<211> LENGTH: 13
<212> TYPE: PRT
<213> ORGANISM: Artificial Sequence
<220> FEATURE:
<223> OTHER INFORMATION: synthetic substituted NAP peptide (NAP-IBA)
<220> FEATURE:
<221> NAME/KEY: MOD_RES
<222> LOCATION: (6)...(10)
<223> OTHER INFORMATION: Xaa = alpha-aminoisobutyric acid (IBA)

<400> SEQUENCE: 6

Leu Gly Gly Asn Ala Xaa Val Ser Ile Xaa Gln Gln Ser
 1               5                   10

<210> SEQ ID NO 7
<211> LENGTH: 15
<212> TYPE: PRT
<213> ORGANISM: Artificial Sequence
<220> FEATURE:
<223> OTHER INFORMATION: synthetic substituted NAP peptide (NAP-IBA)
<220> FEATURE:
<221> NAME/KEY: MOD_RES
<222> LOCATION: (8)...(12)
<223> OTHER INFORMATION: Xaa = alpha-aminoisobutyric acid (IBA)

<400> SEQUENCE: 7

Leu Gly Leu Gly Gly Asn Ala Xaa Val Ser Ile Xaa Gln Gln Ser
 1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: synthetic substituted NAP peptide (NAP-IBA)
<220> FEATURE:
<221> NAME/KEY: MOD_RES
<222> LOCATION: (11)...(15)
<223> OTHER INFORMATION: Xaa = alpha-aminoisobutyric acid (IBA)

<400> SEQUENCE: 8

Ser Val Ala Leu Gly Leu Gly Gly Asn Ala Xaa Val Ser Ile Xaa Gln
 1               5                   10                  15

Gln Ser

<210> SEQ ID NO 9
```

-continued

```
<211> LENGTH: 5
<212> TYPE: PRT
<213> ORGANISM: Artificial Sequence
<220> FEATURE:
<223> OTHER INFORMATION: synthetic 1-R moiety of substituted NAP peptide
      (NAP-IBA)

<400> SEQUENCE: 9

Leu Gly Leu Gly Gly
 1               5

<210> SEQ ID NO 10
<211> LENGTH: 6
<212> TYPE: PRT
<213> ORGANISM: Artificial Sequence
<220> FEATURE:
<223> OTHER INFORMATION: synthetic peptide derived from beginning of
      third microtubule binding repeat of tau protein

<400> SEQUENCE: 10

Val Gln Ile Val Tyr Lys
 1               5

<210> SEQ ID NO 11
<211> LENGTH: 9
<212> TYPE: PRT
<213> ORGANISM: Artificial Sequence
<220> FEATURE:
<223> OTHER INFORMATION: synthetic activity-dependent neuroprotective
      protein (ADNP) activity dependent neurotrophic
      factor 1 (ADNF-1) active core site, ADNF-9

<400> SEQUENCE: 11

Ser Ala Leu Leu Arg Ser Ile Pro Ala
 1               5

<210> SEQ ID NO 12
<211> LENGTH: 88
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (43)...(47)
<223> OTHER INFORMATION: Xaa = branched alkyl amino acid
<220> FEATURE:
<221> NAME/KEY: VARIANT
<222> LOCATION: (49)...(88)
<223> OTHER INFORMATION: Xaa = any naturally occurring amino acid or
      amino acid analog, positions 50-88 may be present or absent

<400> SEQUENCE: 12

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Asn Ala Xaa Val Ser Ile Xaa Gln
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
65                  70                  75                  80
```

```
Xaa Xaa Xaa Xaa Xaa Xaa Xaa Xaa
                85

<210> SEQ ID NO 13
<211> LENGTH: 87
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (42)...(42)
<223> OTHER INFORMATION: Xaa = branched alkyl amino acid
<220> FEATURE:
<221> NAME/KEY: VARIANT
<222> LOCATION: (48)...(87)
<223> OTHER INFORMATION: Xaa = any naturally occurring amino acid or
      amino acid analog, positions 50-88 may be present or absent

<400> SEQUENCE: 13

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Asn Xaa Val Ser Ile Pro Gln Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
                85

<210> SEQ ID NO 14
<211> LENGTH: 87
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (46)...(46)
<223> OTHER INFORMATION: Xaa = branched alkyl amino acid
<220> FEATURE:
<221> NAME/KEY: VARIANT
<222> LOCATION: (48)...(87)
<223> OTHER INFORMATION: Xaa = any naturally occurring amino acid or
      amino acid analog, positions 50-88 may be present or absent

<400> SEQUENCE: 14

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Asn Ala Pro Val Ser Xaa Gln Xaa
        35                  40                  45

Xaa Xaa Xaa Xaa Xaa Xaa Xaa Xaa Xaa Xaa Xaa Xaa Xaa Xaa Xaa
    50                  55                  60
```

```
Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa
                 85

<210> SEQ ID NO 15
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (3)...(7)
<223> OTHER INFORMATION: Xaa = branched alkyl amino acid
<220> FEATURE:
<221> NAME/KEY: VARIANT
<222> LOCATION: (9)...(48)
<223> OTHER INFORMATION: Xaa = any naturally occurring amino acid or
      amino acid analog, positions 10-48 may be present or absent

<400> SEQUENCE: 15

Asn Ala Xaa Val Ser Ile Xaa Gln Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 16
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (2)...(2)
<223> OTHER INFORMATION: Xaa = branched alkyl amino acid
<220> FEATURE:
<221> NAME/KEY: VARIANT
<222> LOCATION: (8)...(47)
<223> OTHER INFORMATION: Xaa = any naturally occurring amino acid or
      amino acid analog, positions 10-48 may be present or absent

<400> SEQUENCE: 16

Asn Xaa Val Ser Ile Pro Gln Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa
         35                  40                  45

<210> SEQ ID NO 17
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (6)...(6)
<223> OTHER INFORMATION: Xaa = branched alkyl amino acid
<220> FEATURE:
<221> NAME/KEY: VARIANT
<222> LOCATION: (8)...(47)
<223> OTHER INFORMATION: Xaa = any naturally occurring amino acid or
      amino acid analog, positions 10-48 may be present or absent
```

```
<400> SEQUENCE: 17

Asn Ala Pro Val Ser Xaa Gln Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (43)...(47)
<223> OTHER INFORMATION: Xaa = branched alkyl amino acid

<400> SEQUENCE: 18

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Xaa Val Ser Ile Xaa Gln
        35                  40                  45

<210> SEQ ID NO 19
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or
      absent
<220> FEATURE:
<221> NAME/KEY: MOD_RES
<222> LOCATION: (42)...(42)
<223> OTHER INFORMATION: Xaa = branched alkyl amino acid

<400> SEQUENCE: 19

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Xaa Val Ser Ile Pro Gln
        35                  40                  45

<210> SEQ ID NO 20
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
```

```
<220> FEATURE:
<221> NAME/KEY: MOD_RES
<222> LOCATION: (47)...(47)
<223> OTHER INFORMATION: Xaa = branched alkyl amino acid

<400> SEQUENCE: 20

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Xaa Gln
        35                  40                  45

<210> SEQ ID NO 21
<211> LENGTH: 88
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (43)...(47)
<223> OTHER INFORMATION: Xaa = alpha-aminoisobutyric acid
<220> FEATURE:
<221> NAME/KEY: VARIANT
<222> LOCATION: (49)...(88)
<223> OTHER INFORMATION: Xaa = any naturally occurring amino acid or
      amino acid analog, positions 50-88 may be present or absent

<400> SEQUENCE: 21

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Xaa Val Ser Ile Xaa Gln
        35                  40                  45

Xaa Xaa Xaa Xaa Xaa Xaa Xaa Xaa Xaa Xaa Xaa Xaa Xaa Xaa Xaa Xaa
 50              55                  60

Xaa Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa
            85

<210> SEQ ID NO 22
<211> LENGTH: 87
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (42)...(42)
<223> OTHER INFORMATION: Xaa = alpha-aminoisobutyric acid
<220> FEATURE:
<221> NAME/KEY: VARIANT
<222> LOCATION: (48)...(87)
<223> OTHER INFORMATION: Xaa = any naturally occurring amino acid or
      amino acid analog, positions 49-87 may be present or absent
```

-continued

```
<400> SEQUENCE: 22

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Asn Xaa Val Ser Ile Pro Gln Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
            85

<210> SEQ ID NO 23
<211> LENGTH: 87
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (46)...(46)
<223> OTHER INFORMATION: Xaa = alpha-aminoisobutyric acid
<220> FEATURE:
<221> NAME/KEY: VARIANT
<222> LOCATION: (48)...(87)
<223> OTHER INFORMATION: Xaa = any naturally occurring amino acid or
      amino acid analog, positions 49-87 may be present or absent

<400> SEQUENCE: 23

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Asn Ala Pro Val Ser Xaa Gln Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
            85

<210> SEQ ID NO 24
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (3)...(7)
<223> OTHER INFORMATION: Xaa = alpha-aminoisobutyric acid
<220> FEATURE:
<221> NAME/KEY: VARIANT
<222> LOCATION: (9)...(48)
<223> OTHER INFORMATION: Xaa = any naturally occurring amino acid or
      amino acid analog, positions 10-48 may be present or absent

<400> SEQUENCE: 24
```

```
Asn Ala Xaa Val Ser Ile Xaa Gln Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 25
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (2)...(2)
<223> OTHER INFORMATION: Xaa = alpha-aminoisobutyric acid
<220> FEATURE:
<221> NAME/KEY: VARIANT
<222> LOCATION: (8)...(47)
<223> OTHER INFORMATION: Xaa = any naturally occurring amino acid or
      amino acid analog, positions 9-47 may be present or absent

<400> SEQUENCE: 25

Asn Xaa Val Ser Ile Pro Gln Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

<210> SEQ ID NO 26
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (6)...(6)
<223> OTHER INFORMATION: Xaa = alpha-aminoisobutyric acid
<220> FEATURE:
<221> NAME/KEY: VARIANT
<222> LOCATION: (8)...(47)
<223> OTHER INFORMATION: Xaa = any naturally occurring amino acid or
      amino acid analog, positions 9-47 may be present or absent

<400> SEQUENCE: 26

Asn Ala Pro Val Ser Xaa Gln Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

<210> SEQ ID NO 27
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
```

-continued

```
<222> LOCATION: (43)...(47)
<223> OTHER INFORMATION: Xaa = alpha-aminoisobutyric acid

<400> SEQUENCE: 27

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Xaa Val Ser Ile Xaa Gln
        35                  40                  45

<210> SEQ ID NO 28
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (42)...(42)
<223> OTHER INFORMATION: Xaa = alpha-aminoisobutyric acid

<400> SEQUENCE: 28

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Xaa Val Ser Ile Pro Gln
        35                  40                  45

<210> SEQ ID NO 29
<211> LENGTH: 47
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (46)...(46)
<223> OTHER INFORMATION: Xaa = alpha-aminoisobutyric acid

<400> SEQUENCE: 29

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Xaa Gln
        35                  40                  45

<210> SEQ ID NO 30
<211> LENGTH: 88
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
```

-continued

<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (43)...(43)
<223> OTHER INFORMATION: Xaa = branched alkyl amino acid
<220> FEATURE:
<221> NAME/KEY: VARIANT
<222> LOCATION: (49)...(88)
<223> OTHER INFORMATION: Xaa = any naturally occurring amino acid or
      amino acid analog, positions 50-88 may be present or absent

<400> SEQUENCE: 30

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Xaa Val Ser Ile Pro Gln
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
            85

<210> SEQ ID NO 31
<211> LENGTH: 88
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (47)...(47)
<223> OTHER INFORMATION: Xaa = branched alkyl amino acid
<220> FEATURE:
<221> NAME/KEY: VARIANT
<222> LOCATION: (49)...(88)
<223> OTHER INFORMATION: Xaa = any naturally occurring amino acid or
      amino acid analog, positions 50-88 may be present or absent

<400> SEQUENCE: 31

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Xaa Gln
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
            85

<210> SEQ ID NO 32
<211> LENGTH: 48
<212> TYPE: PRT
<213> ORGANISM: Artificial Sequence
<220> FEATURE:

```
<223> OTHER INFORMATION: synthetic substituted NAP peptide
<220> FEATURE:
<221> NAME/KEY: MOD_RES
<222> LOCATION: (3)...(3)
<223> OTHER INFORMATION: Xaa = branched alkyl amino acid
<220> FEATURE:
<221> NAME/KEY: VARIANT
<222> LOCATION: (9)...(48)
<223> OTHER INFORMATION: Xaa = any naturally occurring amino acid or
      amino acid analog, positions 10-48 may be present or absent

<400> SEQUENCE: 32

Asn Ala Xaa Val Ser Ile Pro Gln Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

<210> SEQ ID NO 33
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (7)...(7)
<223> OTHER INFORMATION: Xaa = branched alkyl amino acid
<220> FEATURE:
<221> NAME/KEY: VARIANT
<222> LOCATION: (9)...(48)
<223> OTHER INFORMATION: Xaa = any naturally occurring amino acid or
      amino acid analog, positions 10-48 may be present or absent

<400> SEQUENCE: 33

Asn Ala Pro Val Ser Ile Xaa Gln Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

<210> SEQ ID NO 34
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (43)...(43)
<223> OTHER INFORMATION: Xaa = branched alkyl amino acid

<400> SEQUENCE: 34

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Asn Ala Xaa Val Ser Ile Pro Gln
         35                  40                  45

<210> SEQ ID NO 35
```

```
<211> LENGTH: 48
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: VARIANT
<222> LOCATION: (1)...(40)
<223> OTHER INFORMATION: Xaa = any naturally occurring amino acid or
      amino acid analog, positions 2-40 may be present or absent
<220> FEATURE:
<221> NAME/KEY: MOD_RES
<222> LOCATION: (47)...(47)
<223> OTHER INFORMATION: Xaa = branched alkyl amino acid

<400> SEQUENCE: 35

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Xaa Gln
        35                  40                  45

<210> SEQ ID NO 36
<211> LENGTH: 8
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (3)...(7)
<223> OTHER INFORMATION: Xaa = branched alkyl amino acid

<400> SEQUENCE: 36

Asn Ala Xaa Val Ser Ile Xaa Gln
1               5

<210> SEQ ID NO 37
<211> LENGTH: 7
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (2)...(2)
<223> OTHER INFORMATION: Xaa = branched alkyl amino acid

<400> SEQUENCE: 37

Asn Xaa Val Ser Ile Pro Gln
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (6)...(6)
<223> OTHER INFORMATION: Xaa = branched alkyl amino acid

<400> SEQUENCE: 38

Asn Ala Pro Val Ser Xaa Gln
1               5

<210> SEQ ID NO 39
<211> LENGTH: 8
```

```
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (3)...(3)
<223> OTHER INFORMATION: Xaa = branched alkyl amino acid

<400> SEQUENCE: 39

Asn Ala Xaa Val Ser Ile Pro Gln
 1               5

<210> SEQ ID NO 40
<211> LENGTH: 8
<212> TYPE: PRT
<213> ORGANISM: Artificial Sequence
<220> FEATURE:
<223> OTHER INFORMATION: synthetic substituted NAP peptide
<220> FEATURE:
<221> NAME/KEY: MOD_RES
<222> LOCATION: (7)...(7)
<223> OTHER INFORMATION: Xaa = branched alkyl amino acid

<400> SEQUENCE: 40

Asn Ala Pro Val Ser Ile Xaa Gln
 1               5
```